(12) United States Patent
Hawes

(10) Patent No.: US 12,193,514 B2
(45) Date of Patent: *Jan. 14, 2025

(54) ELECTRONIC VAPING DEVICE

(71) Applicant: Altria Client Services LLC, Richmond, VA (US)

(72) Inventor: Eric Hawes, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 162 days.

This patent is subject to a terminal disclaimer.

(21) Appl. No.: 18/148,274

(22) Filed: Dec. 29, 2022

(65) Prior Publication Data

US 2023/0139031 A1 May 4, 2023

Related U.S. Application Data

(63) Continuation of application No. 16/983,045, filed on Aug. 3, 2020, now Pat. No. 11,540,563, which is a
(Continued)

(51) Int. Cl.
*A24F 47/00* (2020.01)
*A24F 40/46* (2020.01)
(Continued)

(52) U.S. Cl.
CPC .............. *A24F 40/50* (2020.01); *A24F 40/46* (2020.01); *A61L 9/037* (2013.01); *B23P 11/00* (2013.01);
(Continued)

(58) Field of Classification Search
CPC .......... A24F 40/40; A24F 40/42; A24F 40/46; A24F 40/50
See application file for complete search history.

(56) References Cited

U.S. PATENT DOCUMENTS 1,915,028 A 6/1933 Meyer-Jagenberg
5,249,586 A 10/1993 Morgan et al.
(Continued)

FOREIGN PATENT DOCUMENTS

CN 202172847 U 3/2012
CN 102753047 A 10/2012
(Continued)

OTHER PUBLICATIONS

International Search Report and Written Opinion dated Jul. 21, 2014 issued in corresponding International Application No. PCT/US2014/023879.
(Continued)

*Primary Examiner* — Eric Yaary
(74) *Attorney, Agent, or Firm* — Harness, Dickey & Pierce, P.L.C.

(57) ABSTRACT

An electronic smoking article, a method of manufacturing an electronic smoking article, and a method of achieving a smoking experience without combusting tobacco are disclosed. The electronic smoking article includes an authenticated first section, which includes an aerosol generation unit having at least one heater; an authenticated second section, which includes a power supply operable to apply voltage to the at least one heater for heating a liquid in at least a portion of the aerosol generation unit to form an aerosol; and a conductive ink circuit embedded within the first and second sections, and wherein the power supply and the aerosol generation unit are electrically connected upon joining the first and second sections, and wherein each of the first and second sections has a portion of the conductive ink circuit.

20 Claims, 3 Drawing Sheets

Related U.S. Application Data continuation of application No. 16/184,449, filed on Nov. 8, 2018, now Pat. No. 10,729,184, which is a continuation of application No. 15/385,070, filed on Dec. 20, 2016, now Pat. No. 10,123,567, which is a continuation of application No. 14/200,646, filed on Mar. 7, 2014, now Pat. No. 9,560,883.

(60) Provisional application No. 61/799,368, filed on Mar. 15, 2013.

(51) Int. Cl.
*A24F 40/50* (2020.01)
*A61L 9/03* (2006.01)
*B23P 11/00* (2006.01)
*C09D 11/52* (2014.01)
*H01C 17/075* (2006.01)
*H05B 1/02* (2006.01)
*A24F 40/10* (2020.01)

(52) U.S. Cl.
CPC ........... *C09D 11/52* (2013.01); *H01C 17/075* (2013.01); *H05B 1/0244* (2013.01); *A24F 40/10* (2020.01); *Y10T 29/49083* (2015.01); *Y10T 29/49826* (2015.01)

(56) References Cited

U.S. PATENT DOCUMENTS

| | | |
|---|---|---|
| 5,322,075 A | 6/1994 | Deevi et al. |
| 5,666,977 A | 9/1997 | Higgins et al. |
| 5,743,251 A | 4/1998 | Howell et al. |
| 6,615,840 B1 | 9/2003 | Fournier et al. |
| 2003/0154991 A1 | 8/2003 | Fournier et al. |
| 2010/0307518 A1 | 12/2010 | Wang |
| 2011/0036346 A1 | 2/2011 | Cohen et al. |
| 2011/0155153 A1 | 6/2011 | Thorens et al. |
| 2011/0168194 A1 | 7/2011 | Hon |
| 2013/0220315 A1 | 8/2013 | Conley et al. |
| 2015/0053217 A1 | 2/2015 | Steingraber et al. |

FOREIGN PATENT DOCUMENTS

| | | |
|---|---|---|
| EA | 200601250 A1 | 12/2006 |
| EP | 2468118 A1 | 6/2012 |
| RU | 124120 U1 | 1/2013 |
| WO | WO-2007/078273 A1 | 7/2007 |
| WO | WO-2013/012157 A1 | 1/2013 |

OTHER PUBLICATIONS

H. Mance, "Could printed electronics be getting a cigarette break?", Financial Times, retrieved from Internet: URL: http://www.ft.com/cm/s/0/247561ba-cc09-11e1-839a-00144feabdc0.htlm#axzz36ynZsMxg, retrieved on Jul. 9, 2014.
Office Action for corresponding Chinese Application No. 201480019783.6 dated Jun. 7, 2017 and English translation thereof.
Second Office Action dated Jan. 26, 2018 issued in Chinese Patent Application No. 201480019783.6.
Chinese Office Action for corresponding Chinese Patent Application No. 201480019783.6 dated Jan. 26, 2018.
Russian Office Action for corresponding Russian Patent Application No. 2015144158/12 dated Feb. 6, 2018.
Office Action for corresponding European Application No. 14714107.1 dated Jul. 11, 2018.
Indian Examination Report dated Jan. 30, 2020 for corresponding Indian Application No. 5562/CHENP/2015.

ELECTRONIC VAPING DEVICE

RELATED APPLICATION(S)

This is a continuation application of U.S. application Ser. No. 16/983,045, filed Aug. 3, 2020, which is a continuation application of U.S. application Ser. No. 16/184,449, filed Nov. 8, 2018, which is a continuation of U.S. application Ser. No. 15/385,070, filed Dec. 20, 2016, which is a continuation of U.S. application Ser. No. 14/200,646, filed Mar. 7, 2014, which claims the priority and benefit of U.S. Application No. 61/799,368, filed Mar. 15, 2013, the entire contents of each of which are incorporated herein by reference.

Working Environment

Electronic smoking articles, such as electronic cigarettes and aerosol generators can include a capillary tube and/or capillary wick designed to deliver liquid material from a liquid reservoir to a heater. Such articles can be activated by a consumer drawing on a mouth piece to deliver an aerosol to the user.

Electronic smoking articles and cigarettes can consist of two pieces, for example, a first unit or piece, which includes a power supply and control unit, and a second unit or piece, which includes a flavor delivery unit. Alternatively, the smoking article can be a three-piece unit, which includes the power supply and control unit, an aerosol generator or aerosol generation unit, and a flavor delivery unit. Each of these parts is optimized to yield consistent performance. Using parts that are not optimized or made from inferior materials can deliver inferior quality output, damage other parts of the device, and damage the reputation of the manufacturer of the smoking article. Accordingly, it would be desirable to control the use of units manufacture and supplied by others and limit the use to genuine parts.

SUMMARY

In accordance with an exemplary embodiment, an electronic smoking article is disclosed, the electronic smoking article comprising: an authenticated first section, which includes an aerosol generation unit having at least one heater; an authenticated second section, which includes a power supply operable to apply voltage to the at least one heater for heating a liquid in at least a portion of the aerosol generation unit to form an aerosol; and a conductive ink circuit embedded within the first and second sections, and wherein the power supply and the aerosol generation unit are electrically connected upon joining the first and second sections, and wherein each of the first and second sections has a portion of the conductive ink circuit.

In accordance with an exemplary embodiment, a method of manufacturing an electronic smoking article is disclosed, the method comprising: embedding a first portion of a conduction ink circuit in an authenticated first section of a smoking article, the first section including an aerosol generation unit having at least one heater; and embedding a second portion of a conduction ink circuit in an authenticated second section, the second section including a power supply operable to apply voltage to the at least one heater for heating a liquid in at least a portion of the aerosol generation unit to form an aerosol.

In accordance with an exemplary embodiment, a method of achieving a smoking experience without combusting tobacco is disclosed, the method comprising: joining an authenticated first section of a smoking article to an authenticated second section of the smoking article, the first section having a first portion of a conduction ink circuit and the second section having a second portion of a conduction ink circuit; and electrically connecting a power supply and an aerosol generation unit of the electronic smoking article upon the formation of a completed conductive ink circuit between the first and second portions of the smoking article, wherein the first section includes the aerosol generation unit having at least one heater and the second section includes a power supply operable to apply voltage to the at least one heater for heating a liquid in at least a portion of the aerosol generation unit to form an aerosol.

BRIEF DESCRIPTION OF THE DRAWINGS

The disclosure is explained below with reference to the exemplary embodiments shown in the drawings. In the drawings.

DETAILED DESCRIPTION

In accordance with an exemplary embodiment, conductive ink based circuits, which are embedded as part of an electronic smoking article are disclosed. The conductive ink based circuits permit the operation of the electronic smoking article only when used with genuine or approved parts. In accordance with an exemplary embodiment, a conductive ink circuit can be embedded across a two-piece design or among a three-piece design such that the circuit, that activates the power supply and the aerosol generation unit, can be activated only when genuine parts are connected together. In accordance with an exemplary embodiment, a conductive ink based circuit can be placed between the flavor unit (or cartridge) and aerosol generation unit or power supply unit, to activate the article when a genuine or approved flavor unit or cartridge is connected to the electronic smoking article.

In accordance with an exemplary embodiment, the conductive ink based circuit can be used to initiate pre-heating of the heater of the electronic smoking article when the user picks up the smoking article for smoking. The preheating of the heater can help to reduce the latency and improve quantity of aerosol delivered during the initial puffs. In addition, control measures can be incorporated to cut off the power supply to the heater, if a puff is not detected, using a puff detector, within a set time period after the initial handling of the smoking article.

Figure 1:
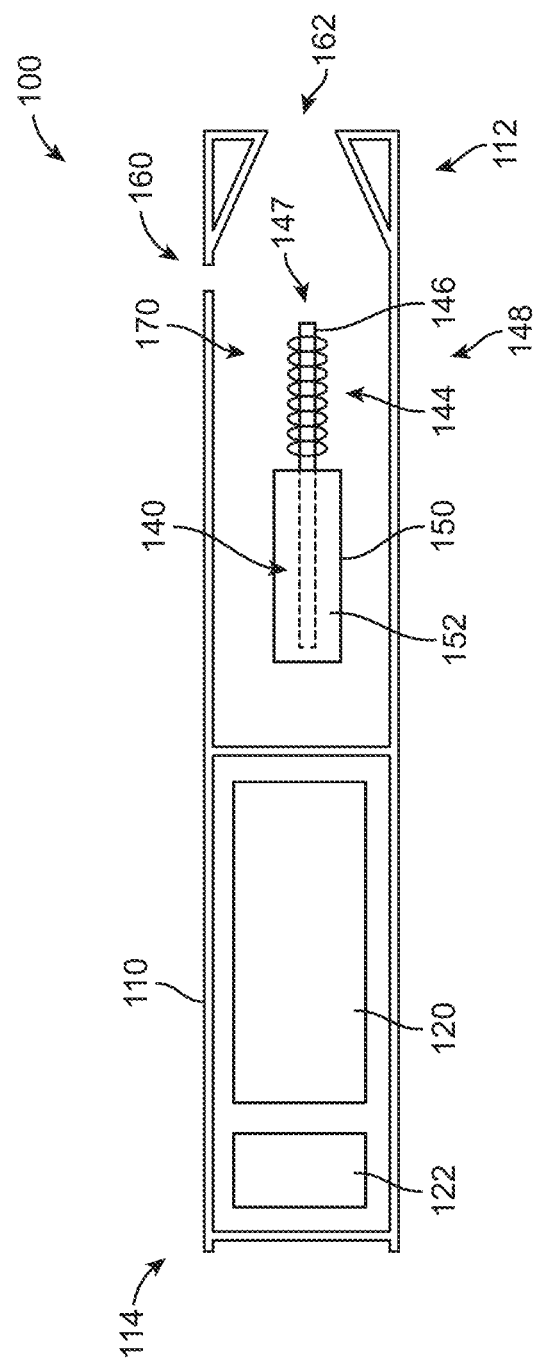
FIG. 1 is a cross-sectional view of an electronic smoking article in accordance with an exemplary embodiment having a conductive ink circuit.

FIG. 1 shows an electronic smoking article 100 in accordance with an exemplary embodiment. As shown in FIG. 1, the electronic smoking article 100 includes a housing 110 having a mouth end 112 and an upstream end 114. In the upstream end 114, there is provided an electric power supply in the form of power supply 120 and electric circuitry in the form of circuitry 122. In the mouth end 112, the smoking article 100 includes a cartridge 140, a heater 144, and a capillary wick (or capillary tube) 146. The cartridge 140, the heater 144, and the capillary wick (or capillary tube) 146 can form the aerosol generation unit 148. In operation, the cartridge 140 delivers a liquid material 152 from a liquid supply reservoir (or fluid reservoir) 150 to the capillary wick 146, which is surrounded by the heater 144. In accordance with an exemplary embodiment, one end of the capillary wick 146 extends to the cartridge 140 and the other end of the capillary wick 146 is surrounded by the heater 144. The heater 144 is connected to the electric circuitry 122 via connections (not shown). The housing 110 also includes an air inlet 160, an outlet 162 at the mouth end 112, and an aerosol forming chamber 170.

In use, the liquid material 152 is supplied from the fluid reservoir 150 to the capillary wick 146, which as shown in FIG. 1 is surrounded by the heater 144. When a user draws on the electronic smoking article 100 at the air outlet 162, ambient air can be drawn through air inlet 160. In accordance with an exemplary embodiment, the electronic smoking article 100 can include a puff detection system (not shown), which is part of the circuitry 122 on the upstream end 114 of the smoking article 100. The puff detection system can sense the puff and can activate the heater 144 and supply the liquid material to the capillary wick 146.

The power supply 120 supplies pulses of energy to the heater 144 to heat the end of the capillary wick 146 surrounded by the heater 144. The liquid material 152 in the outlet end 147 of the capillary wick 146 is vaporized by the heater 144 to create a supersaturated vapor. At the same time, the liquid material 152 being vaporized is replaced by addition liquid material 152 moving along the capillary wick 146.

In accordance with an exemplary embodiment, the supersaturated vapor created is mixed with and carried in the air flow from the air inlet 160. In the aerosol forming chamber 170, the vapor condenses to form an inhalable aerosol, which is carried towards the outlet 162 and into the mouth of the user. The circuitry 122 and the puff detection system (not shown) are preferably programmable. In accordance with an exemplary embodiment, the circuitry 122 and puff detection system can be used to manage the operation of the electronic smoking article 100.

In use, once the capillary wick 146 is heated, the liquid material contained within a heated portion of the capillary wick 146 is volatilized and ejected out of the outlet 147 where it expands and mixes with air and forms an aerosol in a mixing chamber 170. The electronic smoking article 100 also includes at least one air inlet 160 operable to deliver air to the mixing chamber 170. Preferably, the air inlets 160 to the mixing chamber 170 can be arranged downstream of the capillary wick 146 so as to minimize drawing air along the capillary and thereby avoid cooling of the capillary wick 146 during heating cycles.

In use, the volatilized material expands out of the wick 146 and into the mixing chamber 170 where the volatized material can mix with air to form an aerosol which is then drawn through the outlet 162. In an exemplary embodiment, the at least one air inlet 160 includes one or two air inlets 160. Alternatively, the air inlets 160 can be three, four, or five or more. In accordance with an exemplary embodiment, the size and number of air inlets 160 can also aid in establishing the resistance to draw of the electronic smoking article 100.

The power supply 120 can be a Lithium-ion battery or one of its variants, for example a Lithium-ion polymer battery. Alternatively, the power supply 120 may be a Nickel-metal hydride battery, a Nickel cadmium battery, a Lithium-manganese battery, a Lithium-cobalt battery or a fuel cell. In accordance with an exemplary embodiment, the electronic smoking article 100 is usable by a smoker until the energy in the power supply is depleted. Alternatively, the power supply 120 may be rechargeable and can include circuitry (not shown) allowing the battery to be chargeable by an external charging device. For example, the circuitry, when charged, can provide power for a pre-determined number of puffs, after which the circuitry must be re-connected to an external charging device. The electronic smoking article 100 can also include control circuitry 122, which can be on a printed circuit board having a processor.

In accordance with an exemplary embodiment, the liquid material 152 includes a tobacco-containing material including volatile tobacco flavor compounds which are released from the liquid upon heating. The liquid material 152 may also be a tobacco flavor containing material or a nicotine-containing material. Alternatively, or in addition, the liquid material 152 may include a non-tobacco material. For example, the liquid material 152 may include water, solvents, ethanol, plant extracts and natural or artificial flavors. Preferably, the liquid material further includes an aerosol former. Examples of suitable aerosol formers are glycerine and propylene glycol.

In accordance with an exemplary embodiment, the aerosol generation unit includes the liquid supply reservoir 150 and a capillary wick 146 for holding liquid received from the liquid reservoir. In accordance with an exemplary embodiment, rather than a capillary wick 146, the aerosol generation unit 148 can include a capillary tube (not shown) having an inlet and an outlet, the inlet being in communication with the outlet of the liquid supply reservoir, and the at least one heater 144 is operable to heat the capillary tube to a temperature sufficient to at least initially volatilize the liquid material contained within the capillary tube.

The control circuitry 122 can also include a heater activation light (not shown) at an upstream end of the smoking article 100, which is operable to glow when the heater 144 is activated. The control circuitry 122 can also include a timer operable to limit the time for which power is supplied to the heater 144. The time-period of the electric current supply to the heater 144 may be pre-set depending on the amount of liquid material 152 desired to be vaporized. For example, the control circuitry 122 can be programmable for this purpose.

In accordance with an exemplary embodiment, when activated, the heater 144 heats a portion of the wick 146 for less than about 10 seconds, more preferably less than about 7 seconds. Thus, the power cycle (or maximum puff length) can range in period from about 1 second to about 10 seconds.

Figure 2:
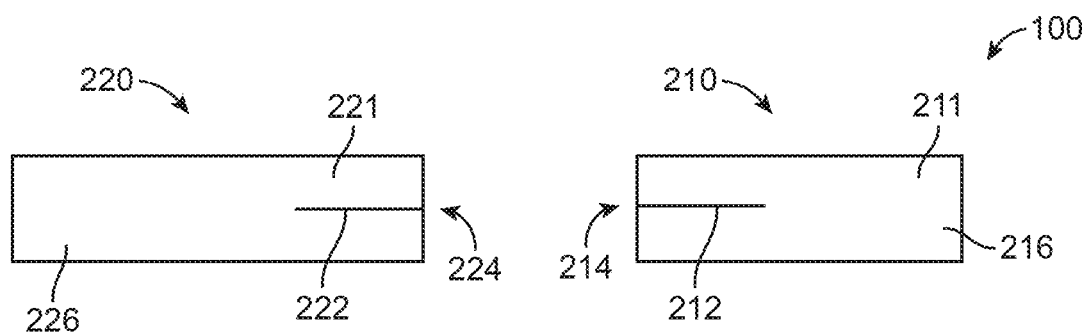
FIG. 2 is a side view of an electronic smoking article in accordance with an exemplary embodiment having a first portion and a second portion, which forms a conductive ink circuit upon assembly thereof.

FIG. 2 is a side view of an electronic smoking article 100 in accordance with an exemplary embodiment having a first section 210 and a second section 220, which forms a conductive ink circuit upon assembly thereof. As shown, the electronic smoking article 100 includes a first section 210, which includes an aerosol generation unit 211 and a second section 220, which includes a power supply portion 221, which can be coupled together at a threaded joint (not shown) or by other convenience such as a snug-fit, snap-fit, detent, clamp and/or clasp.

In accordance with an exemplary embodiment, the aerosol generation unit 211 can include the at least one heater 144, a liquid reservoir 150 having a liquid material 152 therein, and a capillary wick (or capillary tube) 146. The power supply section 221 includes a power supply 120 and circuitry 122, which is operable to apply voltage to the at least one heater 144 for heating the liquid material 152 in at least a portion of the aerosol generation unit 148 to form an aerosol.

In accordance with an exemplary embodiment, a portion 212, 222 of the conductive ink circuit is embedded within the first and second sections 210, 220, respectively, and the power supply and the aerosol generation unit 148 can be activated upon formation of a circuit formed by connecting or coupling the first and second sections 210, 220 to one another. The portions 212, 222 of the conductive ink circuit can be embedded within the outer housing 216, 226 as shown in FIG. 2. Alternatively, the portions 212, 222 can form part of the electrical circuit within the smoking article 100. For example, in accordance with an exemplary embodiment, the conductive ink circuit can be formed by the connection of the first and second sections 210, 220 to form the electrical circuit, which provides power from the power supply 120 to the at least one heater 144 within the aerosol generation unit. Alternatively, the conductive ink circuit formed by the connection of the first and second portions 212, 222 can form a circuit in communication with the circuitry 122 of the smoking article 100, and upon establishing the conductive ink circuit, the circuitry 122 enables the power supply 122 to provide power to the at least one heater 144.

In accordance with an exemplary embodiment, the conductive circuit can be formed by bringing into contact, an end portion 214, 224 of each of the first and second sections 210, 220 to complete the conductive ink circuit.

In accordance with an exemplary embodiment, upon forming the circuit, a pre-heating process of the at least one heater 144 of the smoking article 100 can be initiated. In addition, the pre-heating of the smoking article 100 can also be configured based on detection of a user picking up the smoking article 100. For example, a smoking article 100 having a conductive ink circuit on an outer portion thereof upon detection of being handled by a user, the smoking article 100 can begin a pre-heating process, which can reduce the latency and improve quantity of the aerosol delivered during the initial puffs.

In accordance with an exemplary embodiment, the first section 210 and the second section 220 each comprise an outer cylindrical housing 216, 226 extending in a longitudinal direction, and wherein each of the outer cylindrical housings has a portion 212, 222 of the conductive ink circuit embedded therein.

Figure 3:
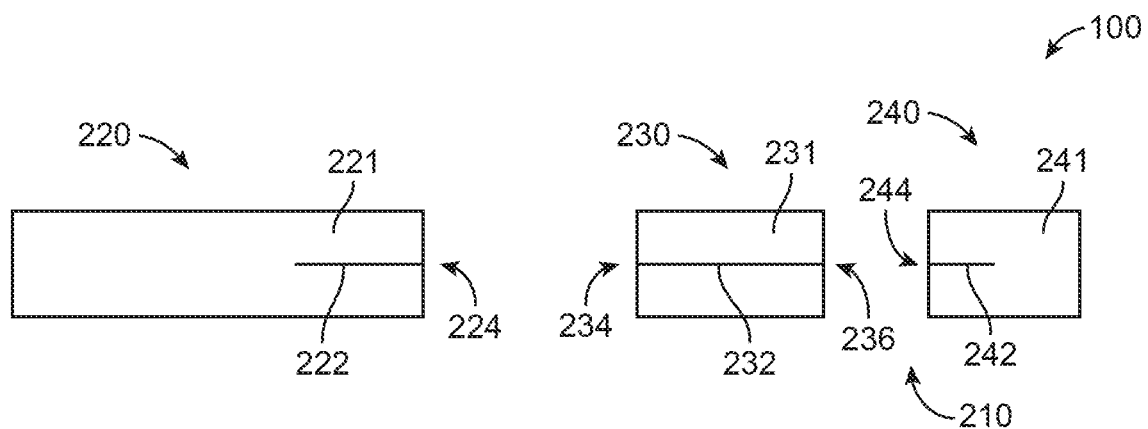
FIG. 3 is a side view of an electronic smoking article in accordance with an exemplary embodiment having a first section, which includes an aerosol generation portion and a liquid supply portion, and a second portion, which forms a conductive ink circuit upon assembly thereof.

FIG. 3 is a side view of an electronic smoking article 100 in accordance with an exemplary embodiment having a two-piece first section 210, which includes an aerosol generation portion 240 and a liquid supply portion 230, and a second portion 220, which forms a conductive ink circuit upon assembly thereof. In accordance with an exemplary embodiment, the first section 210 includes an aerosol generation portion 240 and a liquid supply portion 230, and wherein the conductive ink circuit 242, 232 is embedded within an outer cylindrical housing 241, 231 of the aerosol generation portion 240 and the liquid supply portion 230. The at least one heater 144 housed within the aerosol generation portion 240 is activated only when the conductive ink circuit is formed by connecting the aerosol generation portion 240, the liquid supply portion 230 and the second portion 220, and wherein the aerosol generation portion 240, the liquid supply portion 230 and the second section 210 each has a portion 242, 232, 222. 224, 234, 236, and 244 of the conductive ink circuit and upon assembly thereof forms the circuit.

In accordance with an exemplary embodiment, for example, the conductive ink circuit can be embedded in parts manufactured by an authorized manufacturer of the first and second sections 210, 220 for a two-piece electronic smoking article 100, or an authorized manufacturer of the aerosol generation portion 240, the liquid supply portion 230, and the second portion, for a three-piece electronic smoking article 100. For example, if a user attempts to place a non-authorized part within the smoking article 100, the smoking article 100 will not function. For example, in the absence of the conductive ink circuit, the power supply 120 will not provide power to the heater 144.

Figure 4:
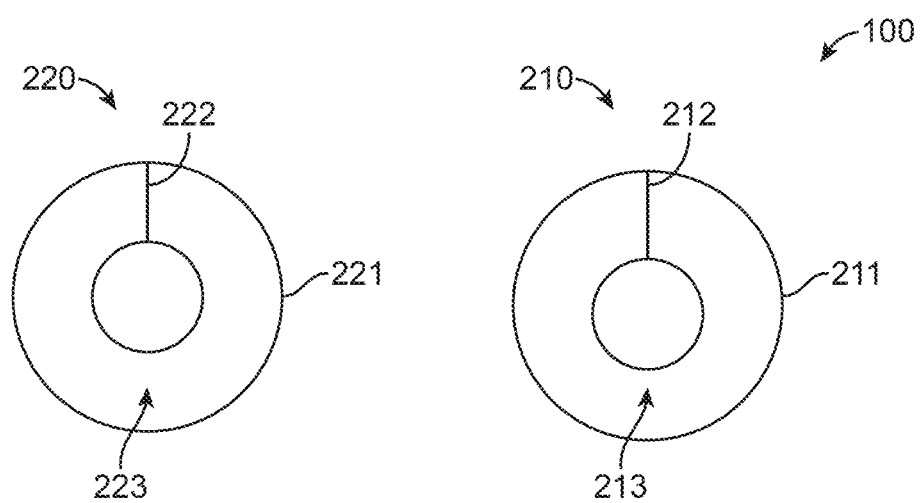
FIG. 4 is an end view of the first portion and the second portion of an electronic smoking article in with an exemplary embodiment having a portion of a conductive ink circuit therein.

FIG. 4 is an end view of the first portion 210 and the second portion 220 of an electronic smoking article in with an exemplary embodiment, wherein each of the first and second portions 210, 220 includes a portion of a complete conductive ink circuit therein. As shown in FIG. 4, the conductive ink circuits 212, 222 can be embedded within the end portions 213, 223, and upon connecting the first and second portions 210, 220 of the smoking article 100, the conductive ink portions 212, 222 complete the circuit. In accordance with an exemplary embodiment, the conductive ink circuits 212, 222 can be elongated line, pattern or completely covered area forming a contact and/or contact pads.

The electronic smoking article 100 is preferably about the same size as a conventional cigarette. In some embodiments, the electronic smoking article 100 can be about 80 mm to about 88 mm long and about 7 mm to about 8 mm in diameter. The outer cylindrical housing 110 of the electronic smoking article 100 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene.

In an exemplary embodiment, the heater 144 includes a coil of wire at least partially surrounding the capillary wick 146. In an exemplary embodiment, the heater 144 is a metal wire and/or a metal alloy wire. The heater 144 can be a coil, which can extend fully or partially along the length of the capillary wick 146.

The electronic smoking article 100 can include a puff indicator (not shown) for indicating when the heater 144 is activated. In the embodiment in which the electric circuitry includes a sensor to detect air flow indicative of a user taking a puff, the indicator, such as an LED, may be activated when the sensor senses air flow indicative of the user taking a puff. In the embodiment in which the electric circuitry includes a manually operable switch, the indicator may be activated by the switch. In addition, control measures can be incorporated to cut off the power supply to the heater if a puff is not detected by a puff detector, within a set time period after the initial handling of the smoking article.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, for example, weight percentages.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features, which meet the strict definitions, but also features, which fairly approximate the strict definitions.

It will now be apparent that a new, improved, and non-obvious electronic smoking article has been described in this specification with sufficient particularity as to be understood by one of ordinary skill in the art. Moreover, it will be apparent to those skilled in the art that numerous modifications, variations, substitutions, and equivalents exist for features of the electronic smoking article, which do not materially depart from the spirit, and scope of the invention. Accordingly, it is expressly intended that all such modifications, variations, substitutions, and equivalents, which fall within the spirit and scope of the invention as defined by the appended claims, shall be embraced by the appended claims.

What is claimed is:

1. An electronic smoking article comprising:
a first housing of the electronic smoking article including a first portion of a conductive ink circuit embedded in the first housing;
a second housing of the electronic smoking article including a second portion of the conductive ink circuit embedded in the second housing, the second housing configured to removably connect to the first housing, and the second portion of the conductive ink circuit configured to removably connect to the first portion of the conductive ink circuit; and
a third housing of the electronic smoking article including a third portion of the conductive ink circuit embedded in the third housing, the third housing configured to removably connect to the second housing, the third portion of the conductive ink circuit configured to removably connect to the second portion of the conductive ink circuit.

2. The electronic smoking article of claim 1, further comprising:
a reservoir configured to contain a liquid; and
at least one heater configured to generate an aerosol from the liquid.

3. The electronic smoking article of claim 2, wherein the at least one heater is included in the first housing; and the reservoir is included in the second housing.

4. The electronic smoking article of claim 2, further comprising:
a wick in fluid communication with the reservoir, the wick configured to supply the liquid for the at least one heater.

5. The electronic smoking article of claim 4, wherein the wick is further configured to supply the liquid for the at least one heater when the first housing and the second housing are connected.

6. The electronic smoking article of claim 2, further comprising:
a power supply configured to provide energy to the at least one heater; and
control circuitry configured to control activation of the electronic smoking article.

7. The electronic smoking article of claim 6, wherein the power supply and the control circuitry are included in the third housing.

8. The electronic smoking article of claim 6, wherein the control circuitry is further configured to enable the power supply to provide energy to the at least one heater when the first portion, the second portion, and the third portion of the conductive ink circuit are connected.

9. The electronic smoking article of claim 6, wherein the control circuitry is further configured to not enable the power supply to provide energy to the at least one heater when the first portion, the second portion, and the third portion of the conductive ink circuit are not connected.

10. The electronic smoking article of claim 6, wherein an electrical circuit is formed between the power supply and the at least one heater when the first portion, the second portion, and the third portion of the conductive ink circuit are connected.

11. An electronic smoking article comprising:
a first portion of a conductive ink circuit;
a second portion of the conductive ink circuit, the second portion of the conductive ink circuit configured to removably connect to the first portion of the conductive ink circuit; and
a third portion of the conductive ink circuit, the third portion of the conductive ink circuit configured to removably connect to the second portion of the conductive ink circuit, and
the first portion, the second portion, and the third portion form an electrical circuit between at least one heater and a power source when the first portion, the second portion, and the third portion are electrically connected.

12. The electronic smoking article of claim 11, further comprising:
a reservoir configured to contain a liquid; and
the at least one heater configured to generate an aerosol from the liquid.

13. The electronic smoking article of claim 12, wherein the first portion is electrically connected to the at least one heater; and
the second portion is electrically connected to the reservoir.

14. The electronic smoking article of claim 12, further comprising:
a wick in fluid communication with the reservoir, the wick configured to supply the liquid for the at least one heater.

15. The electronic smoking article of claim 14, wherein the wick is further configured to supply the liquid for the at least one heater when the first portion and the second portion are electrically connected.

16. The electronic smoking article of claim 12, further comprising:
a power supply configured to provide energy to the at least one heater; and
control circuitry configured to control activation of the electronic smoking article.

17. The electronic smoking article of claim 16, wherein the power supply and the control circuitry are electrically connected to the third portion.

18. The electronic smoking article of claim 16, wherein the control circuitry is further configured to enable the power supply to provide energy to the at least one heater when the first portion, the second portion, and the third portion of the conductive ink circuit are electrically connected.

19. The electronic smoking article of claim 16, wherein the control circuitry is further configured to not enable the power supply to provide energy to the at least one heater when the first portion, the second portion, and the third portion of the conductive ink circuit are not electrically connected.

20. The electronic smoking article of claim 16, further comprising:
   at least one first housing, the at least one first housing including the first portion and the second portion; and
   at least one second housing, the at least one second housing including the third portion.

\* \* \* \* \*